United States Statutory Invention Registration [19]

[11] Reg. Number: H735

Srivastava et al. [43] Published: Feb. 6, 1990

[54] LEAD-203 AS A LABEL FOR RADIOIMAGING

[75] Inventors: Suresh C. Srivastava, Setauket; George E. Meinken, Middle Island, both of N.Y.

[73] Assignee: The United States of America as represented by the United States Department of Energy, Washington, D.C.

[21] Appl. No.: 175,424

[22] Filed: Mar. 30, 1988

[51] Int. Cl.[4] ..... A61K 43/00
[52] U.S. Cl. ..... 424/1.1
[58] Field of Search ..... 424/1.1

[56] References Cited

U.S. PATENT DOCUMENTS 4,348,376 9/1982 Goldenberg ..... 424/1.1
4,421,735 12/1983 Haber et al. ..... 424/1.1
4,732,864 3/1988 Tolman ..... 424/1.1 X

*Primary Examiner*—John F. Terapane
*Assistant Examiner*—Richard Treanor
*Attorney, Agent, or Firm*—Margaret C. Bogosian; James W. Weinberger; Judson R. Hightower

[57] ABSTRACT

A radiopharmaceutical composition comprising a radioactive isotope of lead (Pb-203) in combination with a pharmaceutical or an antibody or antibody fragment and a bifunctional chelating agent. These compositions are especially useful in the imaging and diagnosis of tumors and tumor metastases.

7 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

LEAD-203 AS A LABEL FOR RADIOIMAGING

The U.S. Government has rights in this invention pursuant to contract number DE-AC02-76CH00016 between the U.S. Department of Energy and Associated Universities, Inc.

BACKGROUND OF THE INVENTION

Effective detection and diagnosis of certain disorders such as cancer have long been an object of intense research. The development of targeted pharmaceuticals and monoclonal antibodies has significantly improved the ability to target and deliver diagnostic agents to specific target cells, tissues or organs. Of particular interest in the diagnosis of many forms of carcinoma is the use of antibodies, both polyclonal and monoclonal, to specifically bind to tissues or molecules. The use of such antibodies continues to be an important tool in cancer detection through imaging. To be useful for such imaging purposes, pharamaceuticals and antibodies must first be labeled with an appropriate radionuclide.

Efficient labeling of antibodies, especially monoclonal antibodies, depends on a number of factors, including the characteristics of the radionuclide itself and the method and manner of its incorporation into the protein. The chemical changes inherent in the labeling procedures often cause significant effects on the functional integrity of antibodies and their fragments. To date, most labeling studies for radioimmunoimaging have been carried out with iodine or indium radionuclides. Radiometal labeling of antibodies via the bifunctional chelate approach helps avoid the deleterious effects of oxidation experienced in common iodination reactions. Labeling with metals also overcomes the problems of in vivo deiodination by tumor and normal tissues, particularly when using rapidly internalized antibodies.

The experience with I-131 as the antibody radiolabel has shown that it has several disadvantages, the most significant being high gamma energy, in vivo deiodination, high radiation background, the need for late imaging and the need to use a relatively high radiation dose. Use of In-111 rather than I-131 as the radiolabel for imaging overcomes some of the problems with I-131 because of its good tumor uptake and good imaging photons; however, In-111 presents disadvantages that limit the value of its use. These include the chemistry difficulties presented by this radionuclide, the slow blood clearance of In-111, the high liver and whole body retention of the nuclide, which increases radiation dose and makes it difficult to localize liver metastases, the need to do late imaging, and the fact that SPECT imaging is suboptimal due to decreased photon availability at 3-6 days after injection.

The present invention covers the use of the radionuclide lead-203 as an alternative to I-131 or In-111 for pharmaceutical and antibody labeling for radioimaging in order to overcome the disadvantages associated with I-131 and In-111. Pb-203 possesses good imaging photons and, when used as an antibody label, exhibits good tumor uptake, higher residence time in tumor, good tumor to background ratios, early imaging and SPECT imaging feasibility, the ability to localize liver metastases and faster blood and whole body clearance.

In the present invention, antibodies or active antibody fragments are covalently combined with the radionuclide lead-203. These Pb-203/antibody conjugates retain the antibody specificity and activity, and are useful in diagnostic techniques. The Pb-203/antibody conjugates of the present invention exhibit improved biodistribution and other characteristics in comparison to the most widely used radionuclides, indium-111 and iodine-131.

The superiority of the present invention over known compositions rests in the discovery that Pb-203, which has favorable nuclear and chemical properties, displays superior in vivo behavior when used as a label for pharmaceuticals, antibodies and antibody fragments. In this regard, Pb-203 serves as an alternate and better radiolabel for immunoscintigraphy due to its high tumor uptake and relatively rapid clearance from the blood, liver, and whole body, in contrast to the high blood and liver retention associated with the use of indium-111. The production routes to Pb-203 include:

$$^{203}\mathrm{Tl}(\mathrm{d},2\mathrm{n})^{203}\mathrm{Pb}(23\ \mathrm{MeV})$$

$$^{209}\mathrm{Bi}(\mathrm{p},2\mathrm{p}5\mathrm{n})^{203}\mathrm{Pb}(\mathrm{approx.}\ 50\ \mathrm{MeV})$$

$$^{nat}\mathrm{Pb}(\mathrm{p},\mathrm{xn})^{203}\mathrm{Bi} \xrightarrow{\beta} {}^{203}\mathrm{Pb}(>42\ \mathrm{MeV})$$

Pb-203 decays by electron capture (emitting no betas) with a primary emission of 279 KeV (77%), suitable for imaging. The chemistry of lead (II) is favorable for attachment through chelation techniques to a variety of ligands with diverse functional groups and structures.

It is an object of the present invention to provide a composition comprising Pb-203 bonded to a pharmaceutical or covalently bonded to an antibody or antibody fragment. The covalent bond involves the use of a bifunctional chelating agent.

The 2.17 day half-life of the Pb-203 conjugate herein described is also compatible with another object of the present invention, limiting extended doses of radiation to the patient, particularly in situations in which delayed imaging or emission is either necessary or desirable.

It is also an object of the present invention to provide a Pb-203 conjugate in which many radionuclides may be coupled to an antibody or antibody fragment.

Although tumor imaging and diagnosis is one application of the Pb-203/antibody conjugates, antibodies to a variety of other antigens broaden their usefulness. For example, antibodies to blood cells, fibrin, viruses, and specific tissues, can be conjugated to Pb-203 and used to image and detect clots, abscesses, inflammations, phlebitis, embolisms, and other viral infections and organ abnormalities.

DETAILED DESCRIPTION OF THE INVENTION

The present invention is a radiopharmaceutical composition comprising a radioactive isotope of lead (Pb-203) in combination with a pharmaceutical or an antibody or antibody fragment and a bifunctional chelating agent.

No-carrier-added lead-203 (NCA Pb-203) is commercially available from Atomic Energy of Canada, Ltd., as a lead chloride solution in 0.1 N HCl. Also within the scope of the present invention is the use of radioactive lead nitrate, prepared by drying an aliquot of NCA Pb-203, followed by the addition of a small quantity of concentrated $HNO_3$, and dilution with saline (final pH approx. 4.0).

Lead-203 has very favorable nuclear and chemical properties (tl/2 52 hours, 279 KeV gamma energy, no betas, good coordination chemistry), and is covalently bonded to monoclonal antibodies. The resulting conjugate, administered through intravenous injection of the Pb-203/antibody conjugate has been used in vivo to image and diagnose animal tumors.

The development and production of monoclonal antibodies is well known and has been extensively discussed. A useful reference for obtaining monoclonal antibodies is Koprowski et al., U.S. Pat. No. 4,196,265. The present invention includes the use of any monoclonal antibody which exhibits cell binding or antigen binding capability. The selection and production of suitable monoclonal antibodies is within the skill of the art.

The antibody or antibody fragment used in this invention may be any polyclonal or monoclonal antibody or antibody fragment which forms an immunochemical reaction with an antigen. An "antigen" is a term of art denoting any substance or molecule which induces the formation of an antibody (i.e., that can trigger an immune response), and can be a virus, a bacterium, a fungus, a parasite, tissues or cells not naturally a member of a host's family of tissues or cells, or even a portion or product of any of these organisms. "Antigenic" or "immunogenic" are used to describe the capacity of a given substance to stimulate the production of antibodies.

"Antibody" is a term of art denoting the soluble substance or molecule secreted or produced by an animal in response to an antigen, and which has the particular property of combining specifically with the antigen which induced its formation. Antibodies, also known as immunoglobulins, are classified into five distinct classes——IgG, IgA, IgM, IgD, and IgE. The basic IgG immunoglobulin structure consists of two identical light polypeptide chains and two identical heavy polypeptide chains (linked together by disulfide bonds). When IgG is treated with the proteolytic enzyme papain, an antigen binding fragment can be isolated, termed Fab. When IgG is treated with pepsin (another proteolytic enzyme), a larger fragment is produced, $F(ab')_2$. This fragment can be split in half by reduction to Fab'. The Fab' fragment is slightly larger than the Fab and contains one or more free sulfhydryls from the hinge region (which are not found in the smaller Fab fragment). The term "antibody fragment" is used herein to define the portion known as Fab'. It is well known in the art to treat antibody molecules with pepsin in order to produce antibody fragments [Gorevic et al., *Methods of Enzymol.,* 116:3 (1985)]. The selection of the antibody for the practice of this invention will depend upon the end use for which the Pb-203/antibody conjugate will be employed. Such selection is within the skill in the art.

Antibodies useful in the present invention, include but are not limited to anti-tumor antibodies of human, mouse and rat origin, the various presently used murine monoclonal antibodies including the anticolon carcinoma antibody 17-1A (IgG and $Fab'_2$), other antibodies against tumor associated antigens, and antibodies against various tissue antigens including blood cell antigens. This shows that the labeling procedure of the present invention is generally applicable to a broad range of antibodies and antibody fragments.

The antibodies are generally maintained in an aqueous solution that contains an ionic compound. A physiologic normal saline is preferred and widely available. Other ionic solutions, such as those containing sodium or potassium phosphate, sodium carbonate and the like, are known in the art and may also be used in the practice of this invention.

In one embodiment of the invention, lead-203 is covalently bonded to a monoclonal antibody (such as 17-1A) using a bifunctional chelating agent. Bifunctional chelating agents include but are not limited to derivatives and/or mono- or dicyclic anhydrides of DTPA (diethylenetriamine pentaacetic acid), CYEDTA (trans-1,2-diaminocyclohexane-N,N,N',N'-tetraacetic acid), various other aminopolycarboxylates, tartrates, citrates, EDTA, IDA, TETA and bleomycin. All of these chelating agents may be used in various buffers and many are well known to the practitioner.

The preferred methods of preparing the Pb-203/antibody conjugates are described in Hnatowich et al., *Science,* 220:613 (1983); Srivastava et al., *Int. J. Biol. Markers,* 1:111 (1986); and Meares, *Nucl. Med. Biol.,* 13:311 (1986). Generally, the chelate conjugated to the monoclonal antibody is a derivative of the chelate bonded to an organic functional group which serves to link the chelate to the monoclonal antibody Reacting the chelate derivative and the monoclonal antibody produces the chelate conjugated monoclonal antibodies which can be reacted with lead-203 chloride or lead-203 nitrate to produce the lead-203/antibody conjugates. Purifying the resulting aqueous solution (by HPLC, Centricon filtration, or Sepharose 6B chromatography, for example), yields equal to or greater than 60% of Pb-203/antibody can be obtained. These conjugates retain sufficient activity and selectivity of the antibody or antibody fragment.

The present invention contemplates an in vivo diagnostic procedure which comprises introducing the Pb-203/antibody conjugate of the present invention into the body of a mammal, and allowing sufficient time for the conjugate to localize before imaging. The present invention also contemplates in vitro analytical procedures employing a Pb-203/antibody conjugate.

The present invention also contemplates the use of Pb-203 for labeling pharmaceuticals that require an intermediate half-life for in vivo studies. Pb-203 could replace Tc-99m for those studies where a longer half-life is useful, such as with hepatobiliary agents like HIDA where certain diagnostic procedures require long imaging periods.

The conjugates of this invention may be administered in vivo in any pharmaceutically suitable carrier. A physiologic normal saline solution can be used, and may optionally include an appropriate amount of carrier protein, such as human serum albumin (for antibody stabilization). The appropriate concentration of any biologically active material in a carrier is routinely determined by practitioners in the art.

As has been described above, this invention encompasses many Pb-203/antibody conjugates, with the choice of the antibody depending upon the end use of the Pb-203/antibody conjugate. The radioactive lead atoms decay with emission of a gamma ray, thus permitting imaging of the tissue or organ where the Pb-203/antibody conjugate has localized. For example, Pb-203 conjugated to 17-1A monoclonal antibody is useful for the detection of primary and metastatic human and murine colon carcinoma.

The compositions of the present invention may be administered in any convenient method for introducing foreign substances into the blood stream of mammals. The Pb-203/antibody conjugates of the present invention may be diluted with conventional pharmaceutical carriers for administration into the subject. Intravenous injection is preferred although in some cases subcutaneous, intralymphatic, intraperitoneal or intraarterial injections may provide better results. Diagnostic methods may be in vivo or in vitro.

The following examples are included for illustrative purposes only and are not intended to limit the scope of the invention.

EXAMPLE 1

The anticolon carcinoma antibody 17-1A (IgG2a) was used initially as a model in these studies. Conjugates of 17-1A with DTPA and cyclohexyl EDTA were prepared using the monocyclic or bicyclic anhydride method. The conjugate with TTHA (triethylene tetraamine hexaacetic acid) was prepared using the hexa-N-hydroxysuccinimide ester of TTHA. The substitution level ranged from an average of 3 molecules of DTPA (2–4), 7 molecules of Cy EDTA, and 2 molecules (1–3) of TTHA per molecule of the antibody. The immunoreactivity of the conjugated antibody preparations remained essentially unchanged at these substitution levels. The purified conjugates were labeled with $^{111}$In in an acetate (0.1 M) citrate (0.02 M) buffer, pH 5, and with $^{203}$Pb at pH 8 in the presence of 0.02 M citrate/0.1 M $NaHCO_3$. The products were purified by reverse phase HPLC on a Zorbax GF-250 column with 0.2 M, pH 7, phosphate as the eluting buffer, and alternately using Centricon C-30 centrifugation/filtration devices. In most cases, Centricon filtration results corresponded with the HPLC results. All $^{203}$Pb-labeled samples were EDTA challenged (10 μl, 10 mM) prior to HPLC separation in order to assure high radiochemical purity. Average labeling yields were 60% ($^{203}$Pb) and 90% ($^{111}$In). Immunoreactivity retention (mean values) from cell-binding assays (SW 948 human colon carcinoma cells) was 44% ($^{111}$In) and 37% ($^{203}$Pb), normalized for a 100% value for the unmodified 17-1A (actual 68%).

EXAMPLE 2

Normal, as well as human colon tumor (SW 948 cells) xenografted nude mice, were injected i.v. with the purified radiolabeled preparations. A similarly treated nonrelevant Ig (H-24B5) of the same isotype was used as control. Other controls included $^{203}$Pb-nitrate and $^{203}$Pb-DTPA. Biodistribution was determined by tissue counting at various periods from 2 to 96 hr following injection. Representative data are summarized in Table 1. The results were similar for $^{203}$Pb-CyEDTA-17-1A (not shown).

TABLE 1

Preliminary Tissue Distribution Data (% Dose Per G) in Mice Following Injection of Pb-203 and In-111 Labeled Compounds[a]

| Compound | Time Post Injection | Blood | Liver | Kidney | Bone | Tumor | Whole Body[b] |
|---|---|---|---|---|---|---|---|
| Pb-203 Nitrate | 2 hr[e] | 5.21 ± 0.065 | 9.87 ± 0.82 | 37.4 ± 8.83 | 9.36 ± 0.47 | 1.47 ± 0.06 | 78 |
| | 24 hr[e] | 7.7 ± 1.5 | 6.0 ± 0.5 | 27.6 ± 1.0 | 12.1 ± 0.7 | 0.4 ± 0.15 | 58 |
| | 48 hr[e] | 1.8 ± 0.32 | 3.34 ± 0.73 | 15.2 ± 1.69 | 13.3 ± 1.05 | 0.44 ± 0.21 | 61 |
| Pb-203-DTPA[c] | 3 hr | 1.09 ± 0.04 | 1.24 ± 0.11 | 5.46 ± 0.26 | 1.00 ± 0.06 | — | 11 |
| | 2 hr[d] | 7.9 ± 0.4 | 10.2 ± 0.6 | 36.9 ± 3.0 | 7.1 ± 0.8 | — | 71 |
| Pb-203-17-1A-DTPA | 24 hr[d] | 5.9 ± 0.5 | 6.3 ± 1.0 | 20.7 ± 2.6 | 9.5 ± 1.1 | — | 54 |
| | 48 hr[d] | 2.00 ± 0.40 | 4.24 ± 1.16 | 12.10 ± 1.41 | 12.00 ± 0.94 | — | 47 |
| | 24 hr[e] | 3.57 ± 0.11 | 5.32 ± 0.15 | 15.3 ± 3.3 | 13.3 ± 0.6 | 12.8 ± 1.2 | 61 |
| | 96 hr[e] | 0.93 ± 0.12 | 2.69 ± 0.42 | 6.32 ± 1.50 | 8.10 ± 0.32 | — | 35 |
| Pb-203-p-n-butyl-HIDA | 5 min | 7.0 ± 2.6 | 21.1 ± 3.2 | 24.7 ± 5.5 | 5.2 ± 0.5 | — | 91 |
| | 120 min | 9.9 ± 1.6 | 18.1 ± 1.4 | 37.5 ± 2.0 | 9.2 ± 1.1 | — | 92 |
| | 2 hr | 32.4 ± 1.1 | 13.9 ± 1.5 | 7.1 ± 0.8 | 2.7 ± 0.3 | — | 115 |
| In-111-17-1A-DTPA | 24 hr | 12.9 ± 1.9 | 17.1 ± 4.4 | 12.2 ± 2.0 | 3.6 ± 0.3 | — | 96 |
| | 24 hr[e] | 10.9 ± 4.5 | 9.4 ± 0.6 | 6.9 ± 1.5 | 4.3 ± 1.1 | 7.8 ± 2.4 | 104 |
| | 48 hr[e] | 7.27 ± 2.41 | 9.02 ± 0.91 | 8.03 ± 0.23 | 4.53 ± 0.86 | 7.49 ± 0.06 | 102 |
| | 96 hr[e] | 1.81 ± 1.0 | 8.46 ± 1.17 | 7.23 ± 1.01 | 4.08 ± 0.90 | 4.54 ± 1.03 | 76 |

[a]Normal BNL mice, n=4, excepted as noted. All data normalized to 25 g body weight.
[b]Percent retention
[c]DTPA: diethylenetriamine pentaacetic acid
[d]n = 7
[e]Nude mice with SW 948 tumor xenografts; n = 3

EXAMPLE 3

Compared to the $^{111}$In-17-1A-DTPA, the $^{203}$Pb-17-1A-DTPA cleared the blood, liver, and whole body faster; however, there was somewhat higher bone and kidney uptake. In normal mice where the antibody had no particular targeting, liver uptake with indium was still very high. Lead-203-DTPA gave the distribution of a rapidly excreted hydrophilic chelate. In tumor xenografted nude mice, the tumor uptake of $^{203}$Pb-17-1A DTPA was 12.8% injected dose per g at 24 hr. The tumor-to-blood (T/B) and tumor-to-liver (T/L) ratios were 3.6 and 2.4, respectively. The localization index (L.I., % ID per g tumor ÷ % ID per g whole body) was 5.25. Comparable values for $^{111}$In-17-1A-DTPA were: T/B=0.72; T/L=0.83; and L.I.=1.88. These results are summarized in Table 2.

TABLE 2

Average Tumor-to-Tissue Ratios in Mice of Radiolabeled 17-1A-DTPA

| | $^{203}Pb$ | $^{111}In$ | | |
|---|---|---|---|---|
| | 24 hr | 24 hr | 48 hr | 96 hr |
| % ID/g Tumor | 12.8 | 7.80 | 7.50 | 4.54 |
| Tumor to Blood | 3.6 | 0.72 | 1.03 | 2.51 |
| Tumor to Liver | 2.4 | 0.83 | 0.83 | 0.54 |
| Localization Index* | 5.25 | 1.88 | 1.83 | 1.49 |

*% ID/g tumor/% ID/g whole body

Since $^{203}$Pb-DTPA does not localize significantly in the bone and kidneys, the high uptake of $^{203}$Pb-17-1A-DTPA in these organs is most likely attributable to free lead (dissociated from conjugated DTPA which may bind lead less strongly than free DTPA). Indeed, the distribution of 203Pb nitrate in the tumor mice (% ID per g) at 48 hr was as follows: blood, 1.8; liver, 3.34; kidney, 15.2; bone, 13.3; whole body retention, 61%.

The "second generation" chelating agents will provide further improvement.

Although the invention is described in connection with certain preferred embodiments, it is to be understood that variations and modifications may be resorted to, as will be apparent to those skilled in the art. Such variations and modifications are to be considered within the purview and scope of the invention as set forth in the following claims.

We claim:

1. A conjugate of Pb-203 and an antibody or an antibody fragment useful in radioimaging.

2. The conjugate of claim 1 wherein said antibody is a monoclonal antibody or a fragment thereof.

3. A radiopharmaceutical composition useful in the imaging and diagnosis of a malignant tumor comprising an antibody or fragment thereof specific to said tumor covalently bound to lead-203.

4. The composition of claim 3 wherein said antibody is a monoclonal antibody of a fragment thereof.

5. A radiopharmaceutical composition useful in the imaging and diagnosis of malignant tumors comprising a tumor specific pharmaceutical labeled with Pb-203.

6. A radiopharmaceutical composition useful in the imaging and diagnosis of blood clots, viral infection, and organ dysfunction comprising a cell, tissue, organ or antigen specific pharmaceutical labeled with Pb-203.

7. A radiopharmaceutical composition useful in the imaging and diagnosis of blood clots, viral infection, and organ dysfunctions comprising a cell, tissue, organ or antigen specific antibody or fragment thereof labeled with Pb-203.

* * * * *